(12) United States Patent
Ishibashi et al.

(10) Patent No.: US 7,336,355 B2
(45) Date of Patent: Feb. 26, 2008

(54) FLUORESCENCE SPECTROSCOPIC APPARATUS

(75) Inventors: Kiyochika Ishibashi, Hachioji (JP); Atsushi Miyawaki, Wako (JP)

(73) Assignees: Riken, Saitama (JP); Olympus Corporation, Tokyo (JP)

( * ) Notice: Subject to any disclaimer, the term of this patent is extended or adjusted under 35 U.S.C. 154(b) by 0 days.

(21) Appl. No.: 11/529,017

(22) Filed: Sep. 28, 2006

(65) Prior Publication Data
US 2007/0024964 A1 Feb. 1, 2007

Related U.S. Application Data

(63) Continuation of application No. PCT/JP05/05770, filed on Mar. 28, 2005.

(30) Foreign Application Priority Data
Mar. 29, 2004 (JP) .............................. 2004-096270

(51) Int. Cl.
*G01N 21/64* (2006.01)
(52) U.S. Cl. ..................... 356/318; 356/417; 250/458.1
(58) Field of Classification Search ................ 356/317, 356/318, 417; 250/458.1, 461.1, 461.2
See application file for complete search history.

(56) References Cited

U.S. PATENT DOCUMENTS

| | | | |
|---|---|---|---|
| 4,100,416 A * | 7/1978 | Hirschfeld | 356/318 |
| 5,784,157 A * | 7/1998 | Gorfinkel et al. | 356/318 |
| 6,139,800 A * | 10/2000 | Chandler | 422/82.08 |
| 2003/0058440 A1 * | 3/2003 | Scott et al. | 356/318 |

FOREIGN PATENT DOCUMENTS

| | | |
|---|---|---|
| JP | 4-215044 | 8/1992 |
| JP | 8-506419 | 7/1996 |
| JP | 2003-329590 | 11/2003 |

OTHER PUBLICATIONS

Masataka Kinjo, "Single molecule detection by fluorescence correlation spectroscopy", Protein, Nucleic Acid, and Enzyme, 1999, vol. 44, No. 9, pp. 1431-1437, together with English translation.

Petra Schwille et al., "Dual-Color Fluorescence Cross-Correlation for Multicomponent Diffusional Analysis in Solution", Biophysical Journal (1997), vol. 72, pp. 1878-1886.

Petra Schwille et al., "A dynamic view of cellular processes by in vivo fluorescence auto- and cross-correlation spectroscopy", Methods 29 (2003), pp. 74-85.

Thorsten Winkler et al., "Confocal fluorescence coincidence analysis: An approach to ultra high-throughput screening", Proc. Natl. Acad. Sci. USA (1999), vol. 96, pp. 1375-1378.

* cited by examiner

*Primary Examiner*—F. L. Evans
(74) *Attorney, Agent, or Firm*—Scully, Scott, Murphy & Presser, P.C.

(57) ABSTRACT

There is provided a fluorescence spectroscopic apparatus includes an exciting optical unit configured to irradiate the same sample area with a plurality of excitation lights of different wavelength bands, an optical unit configured to repeatedly guide fluorescences emitted by the sample in response to the respective excitation lights, to a detection unit, and a calculation unit configured to perform analysis on the basis of a comparison of output signals corresponding to the fluorescences from the detection unit, wherein the exciting optical unit includes an excitation light varying unit configured to intermittently vary the intensity of at least one excitation light.

4 Claims, 5 Drawing Sheets

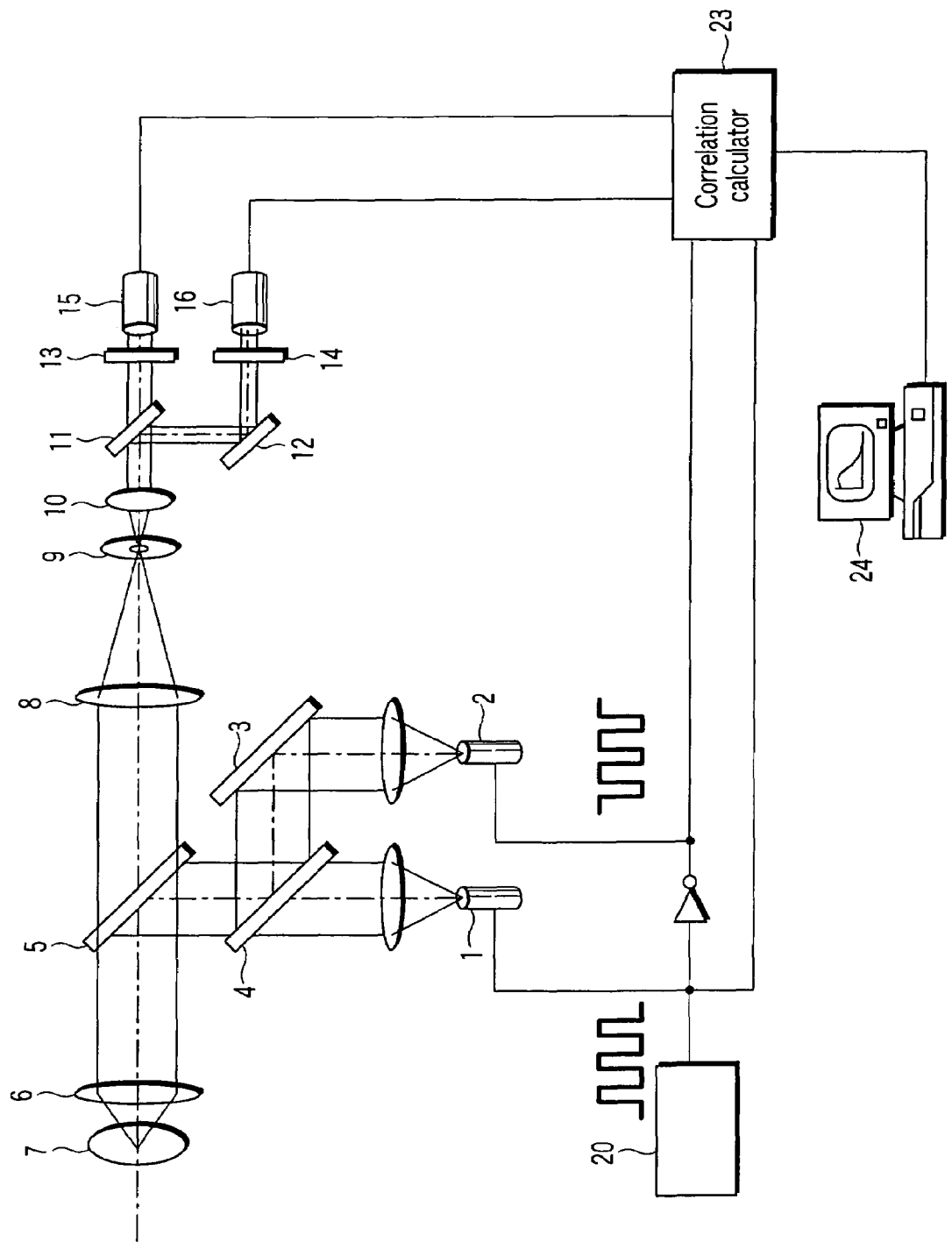
F I G. 2

FLUORESCENCE SPECTROSCOPIC APPARATUS

CROSS REFERENCE TO RELATED APPLICATIONS

This is a Continuation Application of PCT Application No. PCT/JP2005/005770, filed Mar. 28, 2005, which was published under PCT Article 21(2) in Japanese.

This application is based upon and claims the benefit of priority from prior Japanese Patent Application No. 2004-096270, filed Mar. 29, 2004, the entire contents of which are incorporated herein by reference.

BACKGROUND OF THE INVENTION

1. Field of the Invention

The present invention relates to a fluorescence spectroscopy of analyzing a fluctuation in fluorescent molecules in a biological sample to analyze the state of the fluorescent molecules, and a fluorescence spectroscopic apparatus that analyzes the interaction between different fluorescent molecules.

2. Description of the Related Art

Fluorescence correlation spectroscopy (FCS) is a technique for analyzing a fluctuation in light caused by Brownian motion of fluorescent molecules in a fine observation area in a microscopic visual field to determine the autocorrelation function of fluorescence intensity, thus analyzing the diffusion time and average molecular weight for each molecule. Fluorescence correlation spectroscopy is described in, for example, Document 1.

Document 1: "One-Molecule Detection Based on Fluorescence Correlation Spectroscopy" Kinjyō, Protein, Nucleic Acid, and Enzyme, 1999, vol. 44, NO 9, 1431-1438.

Here, when the fluorescence intensity is defined as I(t), the autocorrelation function C(τ) is expressed by Equation (1).

$$c(\tau) = \frac{\langle I(t)I(t+\tau)\rangle}{\langle I(t)\rangle^2} \quad \text{Equation (1)}$$

FIG. 5 is a diagram showing a measuring optical system used for such fluorescence correlation spectroscopy (FCS).

A laser is used as an excitation light source 101 that excites a sample. Laser light from the excitation light source 101 is reflected by a dichroic mirror 102 and enters an objective lens 103. A sample 104 labeled with a fluorescent dye is placed at the focal position of the objective lens 103. Laser light condensed in the focal portion of the objective lens 103 excites the fluorescent dye in the sample to induce fluorescence.

Fluorescence emitted by the fluorescent dye in the sample 104 reaches the dichroic mirror 102 via the objective lens 103. The dichroic mirror 102 has the optical characteristic that it reflects excitation light and allows fluorescence to pass through. The fluorescence from the sample 104 passes through the dichroic mirror 102 and is condensed by a condensing lens 105.

A pinhole 106 is located at the focal position of the condensing lens 105. The pinhole 106 blocks fluorescence from the objective lens 103 except for its focal position to achieve a high space resolution. Those of the fluorescences having passed through the pinhole 106 which are in a desired wavelength band, pass through a barrier filter 108 and enter a photodetector 109. The photodetector 109 measures a fluctuation in fluorescence intensity.

Fluorescence cross-correlation spectroscopy (FCCS) has been proposed which is obtained by expanding such fluorescence correlation spectroscopy (FCS). Fluorescence cross-correlation spectroscopy (FCCS) is a technique for determining the cross-correlation function between fluorescence signals to analyze the association between the signals. Fluorescence cross-correlation spectroscopy (FCCS) is used to, for example, analyze the interaction between molecules labeled with fluorescent dyes in two colors. Fluorescence cross-correlation spectroscopy (FCCS) is described in, for example, Documents 2 and 3 in detail.

Document 2: Dual-Color Fluorescence Cross-Correlation Spectroscopy for Multicomponent Diffusional Analysis in Solution, Petra, Schwille et al, Biophyiscal Journal 1997, 72, 1878-1886.

Document 3: A dynamic view of cellular processes by in vivo fluorescence auto- and cross-correlation spectroscopy, Petra, Schwille et al, Methods 29 (2003) 74-85.

Here, two fluorescent dyes are defined as A and B and their fluorescence intensities are defined as $I_A(t)$ and $I_B(t)$, respectively. A cross-correlation function g(τ) is expressed by Equation (2).

$$g(\tau) = \frac{\langle I_A(t)I_B(t+\tau)\rangle}{\langle I_A(t)\rangle\langle I_B(t)\rangle} \quad \text{Equation (2)}$$

Confocal fluorescence coincidence analysis (CFCA) has also been proposed which detects the coincidence of fluorescence fluctuations in two fluorescent molecules. This technique is described in, for example, Document 4.

Document 4: Confocal fluorescence coincidence analysis (CFCA), Winkler et al., Proc. Natl. Acad. Sci. U.S.A. 96:1375-1378, 1999.

This technique expresses a K value indicating the coincidence by Equation (3).

$$K(n) = \frac{\sum_m N_1(m)N_2(m)}{\sum_m N_1(m)\sum_m N_1(m)} * n \quad \text{Equation (3)}$$

Much attention has been paid to non-aggressive, real-time measurements of these fluorescence spectroscopic methods (FCS, FCCS, and CFCA). In recent years, these methods have been used not only for solutions but also for various biological samples such as cells.

Fluorescence correlation spectroscopy (FCS) detects the presence of interaction on the basis of a variation in diffusion time and is unsuitable for reaction such as the interaction between proteins which does not exhibit a significant variation in diffusion time. On the other hand, fluorescence cross-correlation spectroscopy (FCCS) and confocal fluorescence coincidence analysis (CFCA) are not subject to such a limitation and are thus particularly expected to be applied to analysis of the interaction between proteins.

FIG. 6 is a diagram showing an optical system used for measurements for fluorescence cross-correlation spectroscopy (FCCS) and confocal fluorescence coincidence spectroscopy (CFCA). Optical systems similar to that shown in FIG. 6 are described in, for example, Non-Patent Documents 2, 3, and 4. These measuring optical system use two laser light sources as an excitation light source. For example, a blue laser (wavelength=488 nm) is used as an excitation light source 121. A green laser (wavelength=543 nm) is used as an excitation light source 122.

Laser light from the excitation light sources 121 and 122 is mixed into a single light flux by a dichroic mirror 124. The light flux is reflected by a dichroic mirror 125 and then enters an objective lens 126. A sample 127 is placed at the focal position of the objective lens 126; the sample 127 contains two types of molecules labeled respectively with a fluorescent dye A that is excited by blue excitation light and a fluorescent dye B that is excited by green excitation light.

Fluorescence emitted by the two fluorescent dyes in the sample 127 reaches the dichroic mirror 125 via the objective lens 126. The dichroic mirror 125 has the optical characteristic that it reflects excitation light and allows fluorescence to pass through. The fluorescence from the sample 127 passes through the dichroic mirror 125 and is condensed by a condensing lens 128. A pinhole 129 serves to achieve a high space resolution.

The fluorescence is subsequently separated by a dichroic mirror 131 into the fluorescence emitted by the fluorescent dye A and the fluorescence emitted by the fluorescent dye B. Only the fluorescences that are in desired wavelength bands pass through a barrier filter 133 (for example, passband: 495 to 535 nm) and a barrier filter 134 (for example, passband: 570 to 610 nm). These fluorescences enter photodetectors 135 and 136, respectively. The photodetectors 135 and 136 measure a possible fluctuation in fluorescence intensity.

BRIEF SUMMARY OF THE INVENTION

As shown in FIG. 6, fluorescence cross-correlation spectroscopy (FCCS) generally uses the independent detectors 135 and 136 corresponding to fluorescences in two colors. Specifically, the detector 135 detects the fluorescence only from the fluorescent dye A. The detector 136 detects the fluorescence only from the fluorescent dye B. However, crosstalk occurs between both detectors to some degree. The major cause of the crosstalk is overlapping of emission spectra of the fluorescent dyes.

FIG. 7 is a diagram showing the emission spectra of a fluorescent dye ALEXA488 that is excited by a blue laser and a fluorescent dye TAMRA that is excited by a green laser. The long-wavelength side foot of the fluorescence spectrum of ALEXA488 overlaps the fluorescence wavelength of TAMRA. This indicates that it is impossible to extract only the fluorescence from TAMRA by spectroscopy.

For example, if ALEXA488 and TAMRA are measured using the measurement system shown in FIG. 6, an output from the detector 136 measures a fluorescence fluctuation in the dye TAMRA. However, about 10% of the output measures a fluorescence fluctuation in ALEXA488. As a result, even if no interaction occurs between molecules labeled with ALEXA488 and molecules labeled with TAMRA, an erroneous analysis that about 10% of the molecules interact results.

If the fluorescence spectra of the two-color fluorescent dyes used overlap, possible crosstalk may result in a significant error in the measurement of the cross-correlation function. To avoid an error caused by crosstalk, the wavelengths of the two-color fluorescences are separated from each other as far as possible to reduce their adverse effects. In the example of an optical system introduced in Non-Patent Document 3, excitation light of 488 and 633 nm is used as a combination of such wavelengths. However, an attempt to use fluorescent dyes with separate wavelengths significantly limits the selection of fluorescent dyes.

The present invention has been made in view of these circumstances. An object of the present invention is to provide a fluorescence spectroscopic apparatus that can eliminate the adverse effect of measurement errors caused by crosstalk in spite of overlapping of emission spectra of fluorescent dyes.

A fluorescence spectroscopic apparatus according to an aspect of the present invention comprises an exciting optical unit configured to irradiate the same sample area with a plurality of excitation lights of different wavelength bands, an optical unit configured to repeatedly guide fluorescences emitted by the sample in response to the respective excitation lights, to a detection unit, and a calculation unit configured to perform analysis on the basis of a comparison of output signals corresponding to the fluorescences from the detection unit, wherein the exciting optical unit includes an excitation light varying unit configured to intermittently vary the intensity of at least one excitation light.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a diagram showing the configuration of a fluorescence spectroscopic apparatus according to a second embodiment of the present invention.

DETAILED DESCRIPTION OF THE INVENTION

First Embodiment

Figure 1:
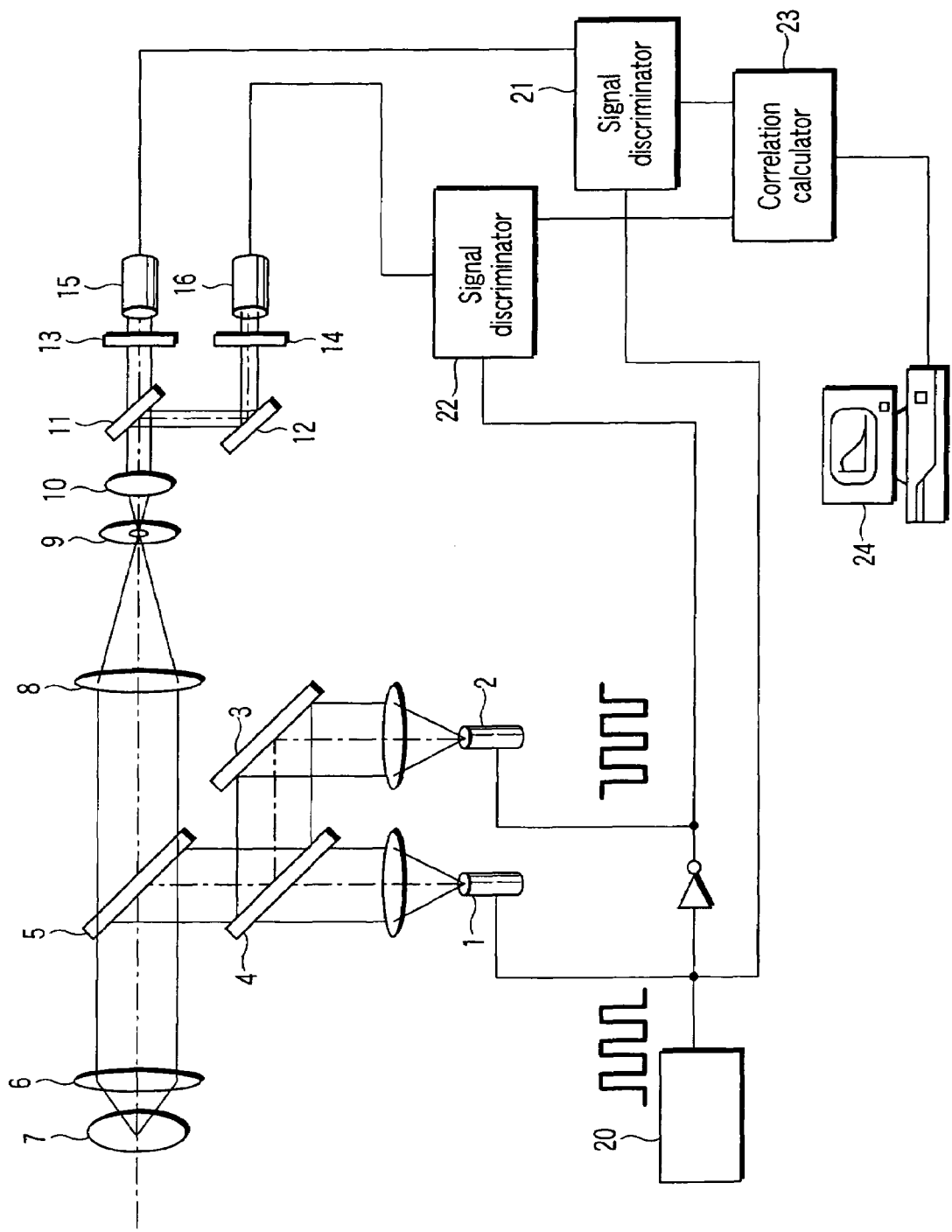
FIG. 1 is a diagram showing the configuration of a fluorescence spectroscopic apparatus according to a first embodiment of the present invention.

FIG. 1 is a diagram showing the configuration of a fluorescence spectroscopic apparatus according to a first embodiment of the present invention.

An excitation light source 1 is a blue laser light source that repeatedly turns on and off laser light at high speed in accordance with signals provided by a switching signal source, to output intermittent laser light. An excitation light source 2 is a green laser light source that repeatedly turns off and on depending on whether the excitation light source 1 is turned on or off, respectively, to output intermittent laser light. This repeated operation is performed at high speed; the operation is repeated at a period of, for example, 1 microsecond.

Intermittent laser light emitted by the excitation light sources 1 and 2 is mixed into a single light flux by a dichroic mirror 4. The light flux is reflected by a dichroic mirror 5 and then enters an objective lens 6. A sample 7 is placed at the focal position of the objective lens 6; the sample 7 contains two types of molecules labeled respectively with a fluorescent dye A that is excited by blue excitation light and a fluorescent dye B that is excited by green excitation light.

The fluorescent dye A is excited by excitation light from the excitation light source 1 to emit fluorescence. On the other hand, the fluorescent dye B is excited by excitation light from the excitation light source 2 to emit fluorescence. Since the excitation light sources 1 and 2 alternately repeat turning on and off, the fluorescent dye A emits fluorescence only while the excitation light source 1 is on. On the other hand, the fluorescent dye B emits fluorescence only while the excitation light source 2 is on. Even after the excitation light is turned off, the fluorescence persists until its lifetime runs out. However, the fluorescence used for fluorescence correlation spectroscopy normally lasts several nanoseconds. Consequently, if the excitation light has a long switching period, the adverse effect of crosstalk is practically negligible.

Fluorescences emitted by the two fluorescent dyes A and B in the sample reach the dichroic mirror 5 via the objective lens 6. The dichroic mirror 5 has the optical characteristic that it reflects the excitation lights and allows the fluorescences to pass through. The fluorescences from the sample 7 pass through the dichroic mirror 5 and pass through a condensing lens 8 and a pinhole 9. The fluorescences are subsequently separated by a dichroic mirror 11 into the fluorescence emitted by the fluorescent dye A and the fluorescence emitted by the fluorescent dye B. The fluorescences that are in desired wavelength bands pass through barrier filters 13 and 14. Detectors 15 and 16 then detect the respective fluorescences.

Here, if the foot of fluorescence spectrum of the fluorescent dye A partly overlaps the fluorescence spectrum of the fluorescent dye B, then the detector 16 provides an output containing not only the fluorescence emitted by the fluorescent dye B but also part of the fluorescence emitted by the fluorescent dye A as a crosstalk component.

Signals from the detector 15 enter a signal discriminator 21. Only the signals output while the laser of the excitation light source 1 is on pass through the signal discriminator 21. Similarly, signals from the detector 16 enter a signal discriminator 22. Only the signals output while the laser of the excitation light source 2 is on pass through the signal discriminator 22.

Since the fluorescent dye A emits fluorescence while the excitation light source 1 is on, the fluorescence detected by the detector 16 and corresponding to a crosstalk component cannot pass through the signal discriminator 2. On the contrary, since the fluorescent dye B emits fluorescence while the excitation light source 2 is on, the fluorescence detected by the detector 15 and corresponding to a crosstalk component cannot pass through the signal discriminator 1.

The signals passing through the signal discriminators 21 and 22 contain only the fluorescences from the fluorescent dyes A and B, respectively. These signals are input to a correlation calculator 23 for cross-correlation calculations. The signals input to the correlation calculator 23 contain no fluorescent crosstalk components. This results in accurate calculations free from crosstalk errors.

The cross-correlation calculation may be executed using intermittent signals output by the signal discriminators 21 and 22. Alternatively, the cross-correlation calculation may be executed using smoothly continuous signals obtained by interpolating the intermittent signals output by the signal discriminators 21 and 22. Further, the cross-correlation calculation may be executed only by the correlation calculator 23 or by the correlation calculator 23 and a processing device 24 which cooperate with each other.

The fluorescence spectroscopic apparatus of the first embodiment achieves accurate calculations free from crosstalk errors. This eliminates the limitation on the selection of fluorescent dyes, thus constructing the optimum measurement environment.

Second Embodiment

FIG. 2 is a diagram showing the configuration of a fluorescence spectroscopic apparatus according to a second embodiment of the present invention. The second embodiment is different from the first embodiment in that the signal discriminators 21 and 22, shown in FIG. 1, are not used but in that these processes are executed by the correlation calculator 23. Accordingly, parts having the same functions as those in the first embodiment are denoted by the same reference numerals, with their detailed description omitted.

Now, description will be given of the operation of the fluorescence spectroscopic apparatus of the second embodiment.

As is the case with the first embodiment, the blue excitation light source 1 and the green excitation light source 2 repeats turning on and off at high speed. Excitation light passes through a path similar to that in the first embodiment and enters the objective lens 6. The sample 7 is then irradiated with the excitation light; the sample 7 contains two types of molecules labeled respectively with the fluorescent dye A that is excited by blue excitation light and the fluorescent dye B that is excited by green excitation light.

Fluorescences emitted by the two fluorescent dyes in the sample 7 pass through a path similar to that in the first embodiment. The fluorescences are then detected by the detectors 15 and 16, which input detection signals to the correlation calculator 23. Signals in synchronism with turn-on and turn-off of the excitation light sources 1 and 2 are input to the correlation calculator 23 by a light source switching signal source 20. A crosstalk component from the fluorescent dye A is contained in the fluorescence signal from the detector 16 which is input to the correlation calculator 23. However, only the signals output when the excitation light source 2 is on are sorted; the sorted signals contain no crosstalk components. Further, a crosstalk component from the fluorescent dye B is contained in the fluorescence signal from the detector 15 which is input to the correlation calculator 23. However, only the signals output when the excitation light source 1 is on are sorted; the sorted signals contain no crosstalk components. Then, correlation calculations based on these signals enable the elimination of crosstalk errors.

The fluorescence spectroscopic apparatus according to the second embodiment not only can exert the effects of the first embodiment but also eliminate the need for signal discriminators to simplify the apparatus configuration. This enables a reduction in apparatus costs.

Third Embodiment

Figure 3:
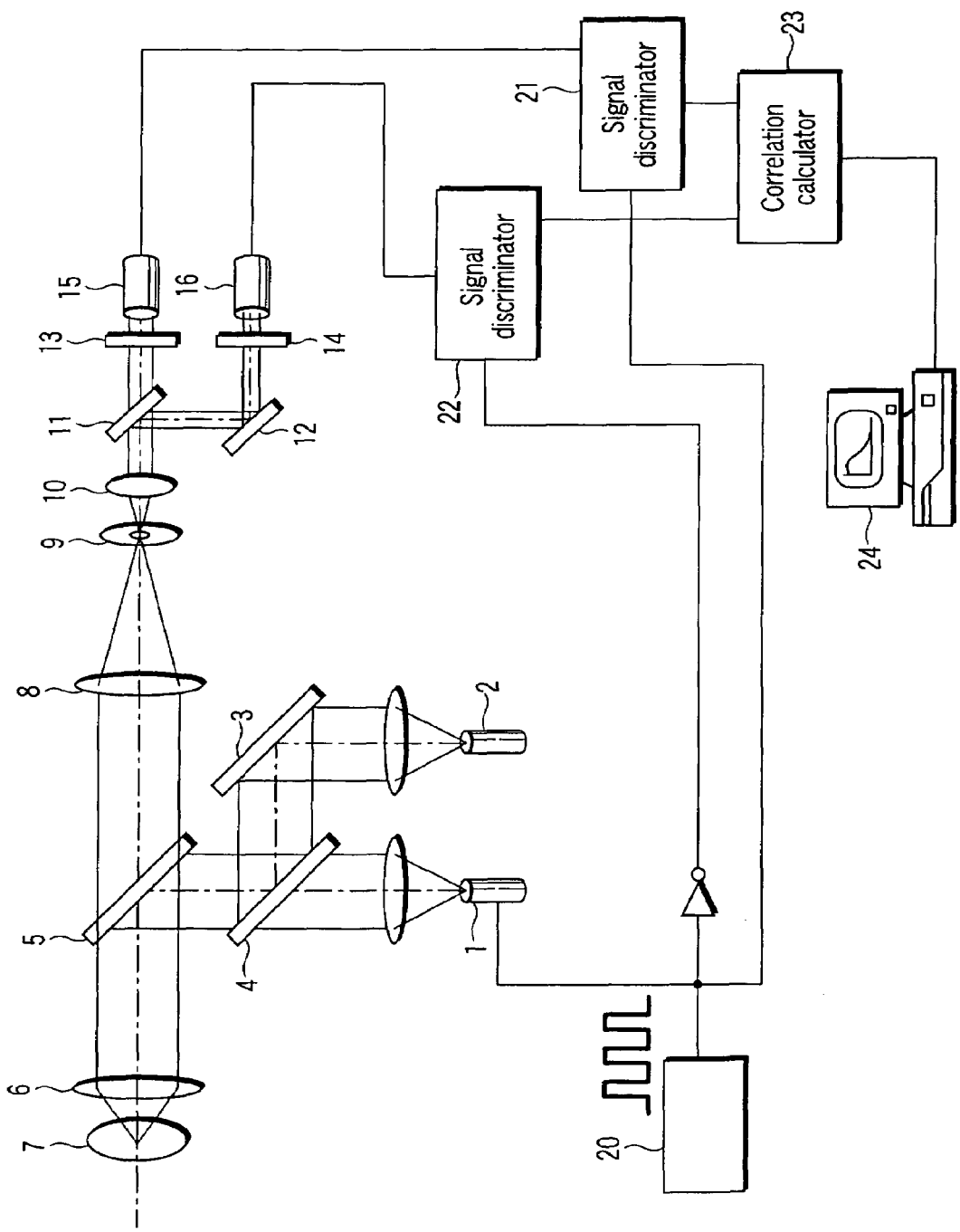
FIG. 3 is a diagram showing the configuration of a fluorescence spectroscopic apparatus according to a third embodiment of the present invention.

FIG. 3 is a diagram showing the configuration of a fluorescence spectroscopic apparatus according to a third embodiment of the present invention. The third embodiment is different from the first embodiment in that the excitation light source 2, shown in FIG. 1, is always on to continuously emit laser light. Accordingly, parts having the same functions as those in the first embodiment are denoted by the same reference numerals, with their detailed description omitted.

Now, description will be given of the operation of the fluorescence spectroscopic apparatus of the third embodiment.

As is the case with the first embodiment, the blue excitation light source 1 repeats turning on and off at high speed in accordance with signals provided by the switching signal source 20. On the other hand, the green excitation light source 2 is always on to continuously emit green excitation light. Excitation light passes through a path similar to that in the first embodiment and enters the objective lens 6. The sample 7 is then irradiated with the excitation light; the sample 7 contains two types of molecules labeled respectively with the fluorescent dye A that is excited by blue excitation light and the fluorescent dye B that is excited by green excitation light. Since the excitation light source 2 is always on, the fluorescent dye B continuously emits fluorescence. On the other hand, the fluorescent dye A emits fluorescence only while the excitation light source 1 is on.

Fluorescences emitted by the two fluorescent dyes in the sample 7 pass through a path similar to that in the first embodiment and are then detected by the detectors 15 and 16.

The foot of fluorescence spectrum of the fluorescent dye A partly overlaps the fluorescence spectrum of the fluorescent dye B. The detector 16 thus provides an output containing not only the fluorescence emitted by the fluorescent dye B but also part of the fluorescence emitted by the fluorescent dye A as a crosstalk component.

The signals from the detector 15 enter the signal discriminator 21. Only the signals output while the laser of the excitation light source 1 is on pass through the signal discriminator 21. Here, since the excitation light source 2 continuously emits light, the fluorescence from the fluorescent dye is also emitted at this timing. However, the appropriate selection of wavelength band of the barrier filter (for example, 495 to 535 nm) allows a barrier filter 13 to remove almost all the fluorescence from the fluorescent dye B. The signal from the detector 15 contains only the fluorescence from the fluorescent dye A.

On the other hand, the signals from the detector 16 enter the signal discriminator 22. Only the signals output while the laser of the excitation light source 1 is off, that is, the signals for the fluorescence from the fluorescent dye B, pass through the signal discriminator 22. The signal discriminators 21 and 22 thus sort the signals for the fluorescences emitted by the fluorescent dyes A and B. The signals are then input to the correlation calculator 23 for cross-correlation calculations. The signals input to the correlation calculator 23 are free from crosstalk components. Consequently, calculations output by the correction calculator 23 are accurate and contain no crosstalk errors.

The fluorescence spectroscopic apparatus according to the third embodiment not only can exert the effects of the first embodiment but also eliminate the need to switch on and off laser light to simplify the apparatus configuration. This enables the apparatus to be inexpensively manufactured.

Figure 4:
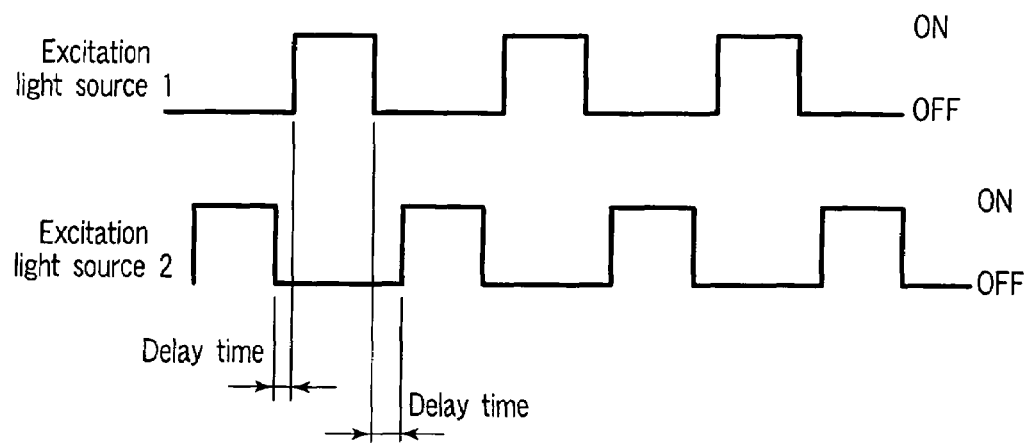
FIG. 4 is a diagram showing switching timings.
Figure 5:
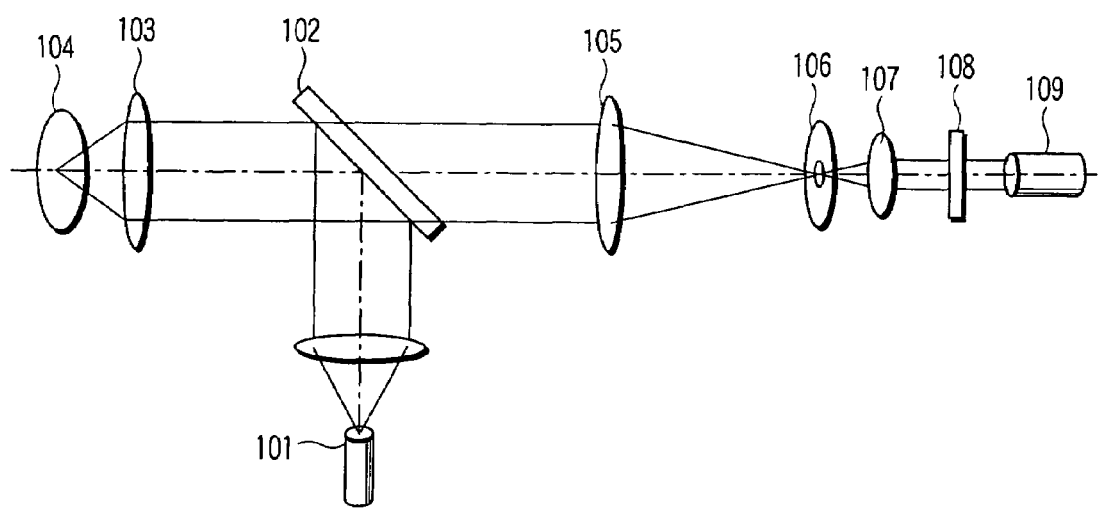
FIG. 5 is a diagram showing a measuring optical system used for fluorescence correlation spectroscopy.
Figure 6:
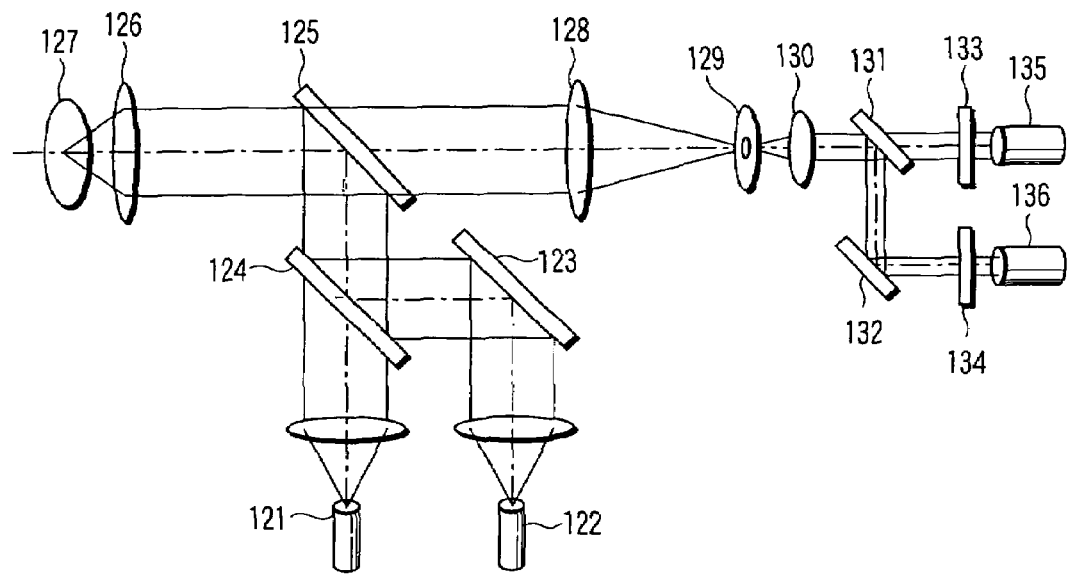
FIG. 6 is a diagram showing an optical system used for measurements for fluorescence cross-correlation spectroscopy and confocal fluorescence coincidence analysis.
Figure 7:
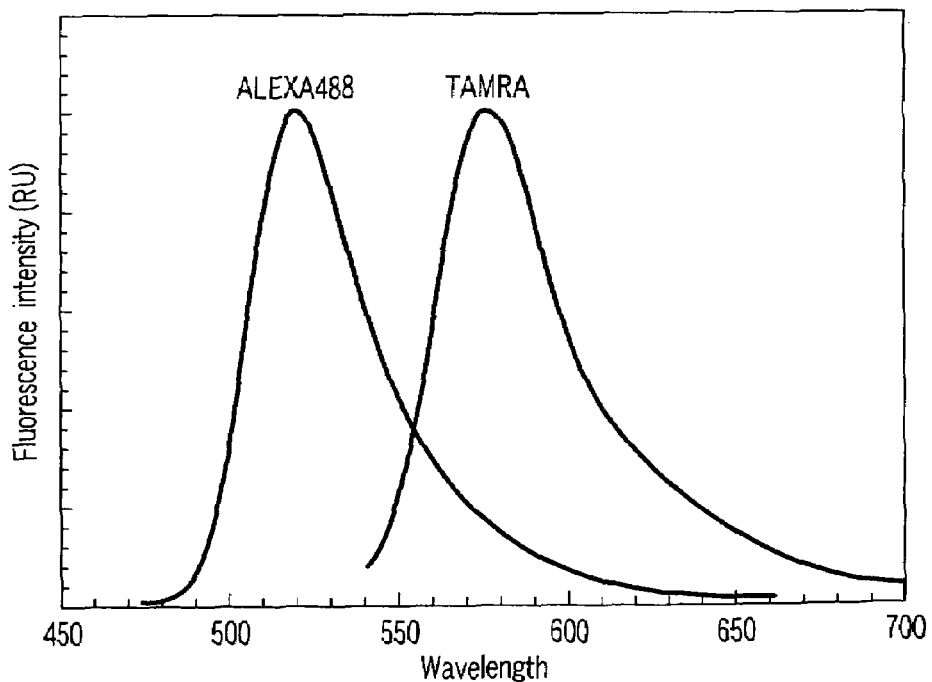
FIG. 7 is a diagram showing the fluorescence spectra of a fluorescent dye excited by a blue laser and a fluorescent dyes excited by a green laser.

The above embodiment shows a switching operation such that immediately after one of the excitation light sources is turned off, the other excitation light source is turned on. However, a delay time may be provided for switching. The fluorescent dyes used for fluorescence correlation spectroscopy generally have a fluorescence lifetime of several nanoseconds. Thus, even after the excitation light is blocked, the fluorescence may persist for a period several times as long as the fluorescence lifetime. Accordingly, the effects of the present invention can further be improved by providing a delay time of at least about 5 nanoseconds for switching to prevent the mixing of fluorescence. FIG. 4 shows switching timings for this case.

In the description of the above embodiment, the switching speed is 1 microsecond. However, the present invention is not limited to this. The switching speed may be selected from a wide range of values. The minimum switching time value is specified on the basis of the fluorescence lifetime. When the delay time for switching is set at 5 nanoseconds to ensure a measurement time of 5 nanoseconds, the minimum period needs to be at least 20 nanoseconds.

The upper limit of the switching speed is specified on the basis of speed of Brownian motion of a measurement target. With a confocal optical system with a high NA (Numerical Aperture), the speed of Brownian motion of fluorescent molecules with a light molecular weight, that is, the diffusion time, is about 50 microseconds. On the other hand, if macromolecules such as protein which have a heavy molecular weight are labeled with fluorescent molecules, the diffusion time may be several hundred milliseconds. The switching time needs to be sufficiently short compared to the diffusion time for molecules to be measured. In view of the above diffusion time, it is virtually difficult to obtain significant data at a switching time of longer than 100 milliseconds.

In the above embodiments, the cross-correlation spectroscopy is described. However, the present invention is similarly applicable to confocal coincidence analysis comprising similar measurement systems using different excitation lights in two colors. That is, "the correlation calculator" in FIGS. 1 to 3 may be replaced with a calculator for coincidence analysis. Therefore, the cross-correlation spectroscopy and confocal fluorescence coincidence analysis may use the same apparatus configuration except for a method for processing data collected from the optical detectors.

The above embodiments describe an example of dyes with a low molecular weight. However, the present invention is not limited to fluorescent dyes of a light molecular weight but is applicable to fluorescent dyes with a heavier molecular weight, for example, fluorescent protein.

The present invention is not limited directly to the above embodiments but may be practiced with constitutional elements thereof modified without deviating from the subject matter of the invention in practical phases. Further, various inventions may be formed by appropriately combining plural constitutional elements disclosed in any of the above embodiments. For example, several constitutional elements may be removed from all constitutional elements suggested in any of the embodiments. Furthermore, constitutional elements may be combined between different embodiments.

What is claimed is:

1. A fluorescence spectroscopic apparatus comprising:
   an exciting optical unit configured to irradiate the same sample area with a plurality of excitation lights of different wavelength bands;
   an optical unit configured to repeatedly guide fluorescences emitted by the sample in response to the respective excitation lights, to respective detection units via respective barrier filters; and a calculation unit configured to perform analysis on the basis of a comparison of output signals corresponding to the fluorescences from the detection units, wherein:

the exciting optical unit comprises an exciting light continuous irradiation unit configured to continuously maintain an intensity of an excitation light, and an excitation light varying unit configured to intermittently vary the intensity of respective excitation light by setting up a delay time so that other plurality of excitation lights do not irradiate each other simultaneously;

respective barrier filters, which intermittent fluorescences occurred by the intermittent excitation lights pass through, are configured to block out fluorescent wavelength bands in which continuous fluorescences occurred by the continuous excitation lights pass through; and the calculation unit performs analysis based on intermittent signals output from the detection units which detected the intermittent fluorescences, and continuous signals output from the detection units which detected the continuous fluorescences.

2. The fluorescence spectroscopic apparatus according to claim 1, wherein the excitation light varying unit varies the intensity of the excitation light in rectangular form.

3. The fluorescence spectroscopic apparatus according to claim 1, wherein the excitation light varying unit varies the intensity of the excitation light with a period of at least 20 nanoseconds and at most 100 milliseconds.

4. The fluorescence spectroscopic apparatus according to claim 1, wherein the analysis is cross-correlation analysis or confocal fluorescence coincidence analysis.

* * * * *